(12) United States Patent
Okamoto et al.

(10) Patent No.: US 8,686,001 B2
(45) Date of Patent: Apr. 1, 2014

(54) MEDICAMENT FOR TREATING GLAUCOMA COMPRISING AS AN ACTIVE INGREDIENT CYCLODEXTRIN-CLATHRATE COMPOUND OF CILOSTAZOL

(75) Inventors: Norio Okamoto, Nishinomiya (JP);
Yoshimasa Ito, Higashiosaka (JP);
Yoshimi Kawakami, Nishinomiya (JP);
Takuji Kurimoto, Nishinomiya (JP);
Noriaki Nagai, Higashiosaka (JP);
Tatsuya Yamashita, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 623 days.

(21) Appl. No.: 12/671,545

(22) PCT Filed: Aug. 1, 2008

(86) PCT No.: PCT/JP2008/064263
§ 371 (c)(1),
(2), (4) Date: May 17, 2011

(87) PCT Pub. No.: WO2009/017259
PCT Pub. Date: Feb. 5, 2009

(65) Prior Publication Data
US 2011/0212993 A1 Sep. 1, 2011

(30) Foreign Application Priority Data

Aug. 2, 2007 (JP) ................................. 2007-202038
Feb. 29, 2008 (JP) ................................. 2008-050466

(51) Int. Cl.
*A61K 31/47* (2006.01)

(52) U.S. Cl.
USPC ......................................... 514/312; 514/913

(58) Field of Classification Search
USPC .................................................. 514/312, 913
See application file for complete search history.

(56) References Cited

U.S. PATENT DOCUMENTS

| 2002/0032171 | A1* | 3/2002 | Chen et al. ........................ 514/54 |
| 2004/0209843 | A1* | 10/2004 | Inoue et al. ...................... 514/58 |
| 2006/0034847 | A1* | 2/2006 | Yun et al. ..................... 424/146.1 |
| 2006/0154963 | A1 | 7/2006 | Hong |

FOREIGN PATENT DOCUMENTS

| EP | 1 396 266 A1 | 3/2004 |
| EP | 1396266 A1 * | 3/2004 |

OTHER PUBLICATIONS

Hotta, et al., "Cilostazol, a selective cAMP phosphodiesterase inhibitor, dilates retinal arterioles and increases retinal and choroidal blood flow in rats", European Journal of Pharmacology, vol. 344, No. 1, XP-00249773, pp. 49-52, (Feb. 26, 1998).
Suzuki, et al., "Effects of Intravenous Cilostazol on Optic Nerve Head and Choroidal Blood Flow in Anesthetized Cats", Journal of Ocular Pharmacology and Therapeutics, vol. 14, No. 3, XP008096302, pp. 239-245, (Jun. 1, 1998).
Iwama, et al., "Neuroprotective effect of cilostazol against retinal ischemic damage via inhibition of leukocyte-endothelial cell interactions", Journal of Thrombosis and Haemostasis, vol. 5, No. 4, XP008096332, pp. 818-825, (Apr. 2007).
International Search Report from the European Patent Office in International Application No. PCT/JP2008/064263 mailed Oct. 10, 2008.

* cited by examiner

*Primary Examiner* — Gigi Huang
(74) *Attorney, Agent, or Firm* — Finnegan, Henderson, Farabow, Garett & Dunner, L.L.P.

(57) ABSTRACT

The invention relates to an ophthalmic medicament for treating glaucoma which comprises a clathrate compound prepared by dissolving cilostazol or a salt thereof in a cyclodextrin.

3 Claims, 4 Drawing Sheets

MEDICAMENT FOR TREATING GLAUCOMA COMPRISING AS AN ACTIVE INGREDIENT CYCLODEXTRIN-CLATHRATE COMPOUND OF CILOSTAZOL

TECHNICAL FIELD

The invention relates to a medicament for treating glaucoma. More particularly, it relates to an ophthalmic medicament for treating glaucoma which comprises a carbostyril derivative of formula (1):

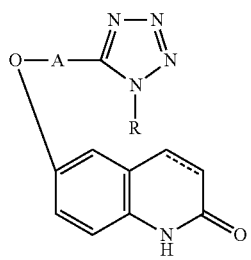

(1)

wherein A is a lower alkylene group, R is a cycloalkyl group, the bonding between 3- and 4-positions of the carbostyril skeleton is a single bond or a double bond, or a salt thereof; and a cyclodextrin.

BACKGROUND ART

Glaucoma is one of the main causes of blindness in Japan and thus it is a severe problem in the ophthalmologic field. According to a previous investigation, patients of glaucoma were estimated at 3.56% among 40- or more aged people. However, a recent big-scaled investigation discloses that even more people are suffering from glaucoma (cf. the website of the Japanese Ophthalmological Society). Glaucoma is thought to be a disease that the intraocular pressure is raised more than normal and then optic nerve is damaged to become visual field constriction which is one of the main causes of blindness.

Recently, normal tension glaucoma has also been becoming a serious problem. The normal tension glaucoma is a disease whose symptom is the same as glaucoma though the intraocular pressure is within the normal range (ordinarily 21 mmHg or less). And it is becoming clear that the prevalence of the normal tension glaucoma covers a large part of the whole glaucoma.

Thus, the cause of glaucoma, especially normal tension glaucoma is not so clear, though glaucoma is a serious disease including a risk factor of blindness, and the classification thereof is also complicated. Therefore, it has been desired to develop a novel medicament for treating glaucoma which is more useful than a current medicament such as a beta-blocker, a prostaglandin drug, and an alpha-agonist; and especially which is expected to have a different mechanism from those of current medicaments or wherein an active ingredient thereof has a different type of structure.

The carbostyril derivatives of formula (1) or salts thereof and the processes for the preparation thereof are disclosed in JP-63-20235-B. And it is known that the carbostyril derivatives (1) have platelet aggregation inhibition action, phosphodiesterase (PDE) inhibition action, antiulcer, hypotensive action and antiphlogistic action, and are useful as an antithrombotic agent, a drug for improving cerebral circulation, an anti-inflammatory agent, an antiulcer drug, an antihypertensive drug, an antiasthmatic drug, a phosphodiesterase inhibitor, etc.

In addition, *Journal of Ocular Pharmacology and Therapeutics* (Vol. 14, No. 3, 239-245 (1998)) discloses that the i.v. injection of cilostazol which is one of the above-mentioned carbostyril derivatives can act on optic nerve, and thus it indicates that the carbostyril derivates might be useful for treating glaucoma without any experimental evaluation.

In addition, JP-2003-63965-A discloses an aqueous formulation of cilostazol for injection which includes a cyclodextrin in order to enhance the solubility of cilostazol to water and then allow cilostazol to be a formulation thereof for injection, since the carbostyril derivatives are hard to dissolve in water.

DISCLOSURE OF INVENTION

Thus, as mentioned above, the cause of glaucoma is not known well, and the classification thereof is complicated. Therefore, it has been desired to develop a more useful medicament for treating glaucoma, especially a novel medicament which does not belong to current types thereof.

The present inventors have intensively studied a new medicament for treating glaucoma, and have found that a clathrate compound prepared by dissolving a carbostyril derivative of the above formula (1), especially 6-[4-(1-cyclohexyl-1H-tetrazol-5-yl)butoxy]-3,4-dihydrocarbostyril (cilostazol) or a salt thereof in a cyclodextrin is useful for treating glaucoma. As mentioned above, although the carbostyril derivative is slightly soluble in water and hence it was not suitable for an ophthalmic drug, an ophthalmic drug comprising the carbostyril derivative has become available by dissolving the carbostyril derivative in a cyclodextrin. Furthermore, it is unexpected that such ophthalmic drug has an action for treating glaucoma, which may be expected as a new type of an ophthalmic medicament for treating glaucoma. In addition, JP-2003-63965-A discloses the use of a cyclodextrin in an injection drug, but not in an ophthalmic drug, and further *Journal of Ocular Pharmacology and Therapeutics* (Vol. 14, No. 3, 239-245 (1998)) indicates that cilostazol which is a carbostyril derivative might be useful for treating glaucoma, but does not disclose any specific pharmacological experiment or any practically exemplified formulation.

The present inventors have found that the ophthalmic administration of a clathrate compound prepared by dissolving 6-[4-(1-cyclohexyl-1H-tetrazol-5-yl)butoxy]-3,4-dihydrocarbostyril (cilostazol) or a salt thereof in a cyclodextrin to a model rabbit suffering from glaucoma can exhibit the improvement for treating glaucoma, which is a first actual medicament for treating glaucoma using the carbostyril derivative, and then have accomplished the present invention.

The present invention provides an ophthalmic medicament for treating glaucoma comprising a carbostyril derivative of the general formula:

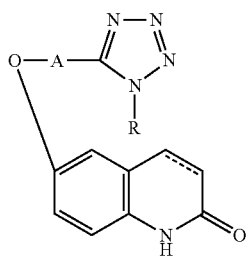

(1)

wherein A is a lower alkylene group, R is a cycloalkyl group, the bonding between 3- and 4-positions of the carbostyril skeleton is a single bond or a double bond, or a salt thereof; and a cyclodextrin.

The present invention also provides an ophthalmic medicament for treating glaucoma comprising 6-[4-(1-cyclohexyl-1H-tetrazol-5-yl)butoxy]-3,4-dihydrocarbostyril (cilostazol) or a salt thereof, and a cyclodextrin.

The present invention also provides the above ophthalmic medicament for treating glaucoma wherein the cyclodextrin is 2-hydroxypropyl-β-cyclodextrin.

The present invention provides an ophthalmic composition comprising the carbostyril derivative (1) or a salt thereof, and a cyclodextrin. Preferable carbostyril derivative is cilostazol, and preferable cyclodextrin is 2-hydroxypropyl-β-cyclodextrin.

The present invention provides a composition for treating glaucoma comprising the carbostyril derivative (1) or a salt thereof, and a cyclodextrin.

The present invention provides the above ophthalmic medicament and composition for treating glaucoma which is a suspension.

The present invention provides use of the above carbostyril derivative (1) and the above cyclodextrin in preparation of a medicament for treating glaucoma.

The present invention provides a method for treating glaucoma which comprises administering an effective amount of the above carbostyril derivative (1) or a salt thereof, and the above cyclodextrin to a patient in need of such treatment.

The present invention provides a medicament for treating glaucoma which comprises administering an ophthalmic drug prepared by dissolving 6-[4-(1-cyclohexyl-1H-tetrazol-5-yl)butoxy]-3,4-dihydrocarbostyril (cilostazol) or a salt thereof in a cyclodextrin. The above "dissolving" means a complete dissolution or a dissolution state suitable for an ophthalmic drug without any trouble. Therefore, a suspension thereof is available if it is suitable for an ophthalmic drug without any trouble.

The present invention provides a medicament for treating glaucoma comprising as an active ingredient the above clathrate compound which is prepared by dissolving carbostyril compound in a cyclodextrin. Herein the clathrate compound means a compound which is thought to form a clathrate complex by taking the above carbostyril derivative into a cyclodextrin via hydrogen binding or other means.

BEST MODE FOR CARRYING OUT THE INVENTION

Figure 1:
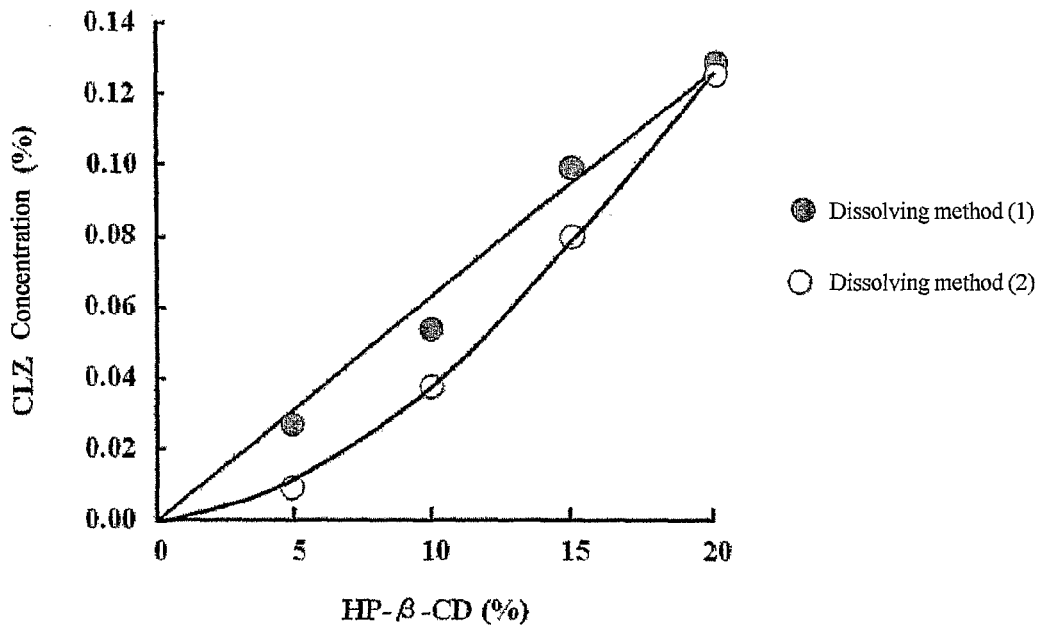
FIG. 1 shows the difference of cilostazol solubility depending on each dissolving method of the ophthalmic clathrate drug of cilostazol in cyclodextrin.

In the above formula (1), the cycloalkyl group includes $C_3$-$C_8$ cycloalkyl groups such as cyclopropyl, cyclobutyl, cyclopentyl, cyclohexyl, cycloheptyl, and cyclooctyl. Preferred cycloalkyl group is cyclohexyl. The lower alkylene group includes $C_1$-$C_6$ alkylene groups such as methylene, ethylene, propylene, butylene, and pentylene, among which preferred one is butylene.

Preferable carbostyril derivative is 6-[4-(1-cyclohexyl-1H-tetrazol-5-yl)butoxy]-3,4-dihydrocarbostyril, which has been put on the market in the trade name of cilostazol as an antiplatelet agent.

The carbostyril derivative (1) can be easily converted to a salt thereof by getting it treated with a pharmaceutically acceptable acid. The acid includes, for example, inorganic acids such as hydrochloric acid, sulfuric acid, phosphoric acid, and hydrobromic acid; and organic acids such as oxalic acid, maleic acid, fumaric acid, malic acid, tartaric acid, citric acid, and benzoic acid.

These carbostyril derivatives (1) and salts thereof and processes for preparation thereof are disclosed, for example, in JP-63-20235-B.

The cyclodextrins of the present invention include cyclodextrins disclosed in JP-2003-63965-A. 2-Hydroxypropyl-β-cyclodextrin (HP-β-CD) is the most preferable, and especially the clathrate compound which the carbostyril derivative (1) or a salt thereof, especially cilostazol, is dissolved therein is useful as a medicament for treating glaucoma because the ophthalmic treatment thereof exhibits markedly decreasing the intraocular pressure without a side effect such as hemolysis.

The clathrate compound is preferably prepared by suspending the carbostyril derivative (1) or a salt thereof, especially cilostazol in a physiological saline and then dissolving the suspension in HP-βCD.

The carbostyril derivative (1) and a salt thereof, especially cilostazol, in the ophthalmic solution may be micronized in order to enhance the solubility thereof or for other purpose, but not limited thereto. It is also possible to make the size thereof in micro-order, or further in nano-order. In addition, the ophthalmic drug comprising the micronized carbostyril derivative may be used in a suspended state or may be used after filtration.

The method for the above micronization includes, for an example of the dryness process, a nano-particulation by micronizing the drug substance of the present invention with strong shearing stress using fluidizing/shredding device, or an impact-type shredding, etc. The method of the wet process includes, for an example, a nano-particulation by suspending the drug substance of the present invention in water or a solution including suspending stabilizer in a moderate concentration, and then subjecting the resultant suspension to micronization using a device such as a stirring mill, a high-pressure homogenizer or a high-pressure-shearing/stirring device. Other method thereof includes a nano-particulation by dissolving the drug substance of the present invention in a supercritical fluid such as carbon dioxide gas, water and ethanol, then releasing it at normal pressures.

The cyclodextrin-clathrate compound of the carbostyril derivative (1) and a salt thereof exhibits a neuroprotective action for retinal ganglion cell. According to the above finding, the compound of the present invention obviously exhibits the therapeutic effect for glaucoma which is an ophthalmic ischemic disease, in addition it is also expected to exhibit the therapeutic effect for other ophthalmic ischemic disease such as retinal vascular occlusion, diabetic retinopathy, ischemic optic neuropathy, ophthalmic ischemic syndrome. Here, the glaucoma includes every kind of glaucoma, but not limited thereto, for example, angle-closure glaucoma, open-angle glaucoma, and congenital glaucoma. With regard to the intraocular pressure of the glaucoma, it also includes ocular hypertension glaucoma and normal tension glaucoma.

The medicament of the present invention for treating glaucoma means, not limited to an eye drop, wide application to eyes such as an ophthalmic solution and an ophthalmic ointment. A formulation for ophthalmic application such as an ophthalmic solution and an ophthalmic ointment can be prepared with a conventional carrier for ophthalmic formulation via a conventional method. The conventional carriers for ophthalmic formulation can be chosen from the substances disclosed in JP-3093661-B.

The present compound of formula (1) may be used in a bulk or preferably in a pharmaceutical formulation prepared with a conventional pharmaceutical carrier or diluent. The concentration of the carbostyril derivative in the formulation is, but not limited to, 0.005 to 1% (w/v), preferably 0.01 to 0.25% (w/v), and in the case of a suspension thereof, 0.1 to 1% (w/v), preferably 0.3 to 0.7% (w/v), more preferably 0.5% (w/v). The concentration of cyclodextrin is 1 to 40% (w/v), preferably 5 to 30% (w/v). The administration thereof is preferably a few drops per a shot, and once to about 10 times a day.

EXAMPLE

Example 1

Process of an Ophthalmic Drug Comprising Cyclodextrin-Clathrate Cilostazol

To 50 mL of physiological saline were added 50 mg of cilostazol (CLZ) and 5 g of cyclodextrin (HP-β-CD), and the mixture was stirred for 30 minutes. However, CLZ of the mixture was not completely dissolved. And then additional HP-β-CD was added several times in an amount of 2.5 g at a time with stirring, and CLZ was completely dissolved when the total amount of HP-β-CD reached 10 g. Thus, a 0.1% CLZ solution (HP-β-CD 20%) was prepared. To the solution was added 50 mL of physiological saline to give a 0.05% CLZ solution (HP-β-CD 10%), which was filtrated for sterilization to give an ophthalmic solution of clathrate compound of CLZ in cyclodextrin. (The above concentrations are shown as weight/volume %.)

Example 2

Process of a Cyclodextrin-Clathrate Suspension Containing Micronized Cilostazol in a High Concentration To 500 mL of physiological saline were added 2.5 g of low-substituted methyl cellulose (MC) and then 25 g of HP-β-CD so that the mixture should be completely dissolved to give 5% HP-β-CD solution containing 0.5% MC. To 300 mL of the solution was added 1.5 g of cilostazol (CLZ) to prepare a suspension thereof, which was put through a microfluidizer (M-110-E/H, MIZUHO INDUSTRIAL CO., LTD) four times. The operation of the passage was carried out under compressed pressure (165 MPa), cooling the flow path of the microfluidizer from outside thereof and monitoring the variation of the particle size in every passage with MT3300 (LOW-WET) measuring device of particle size (Nikkiso). After the 4th passage, the particle size was 1.156 μm as number mean diameter (MN). The suspension and the filtrate of the suspension were termed ophthalmic solution 1 and ophthalmic solution 2, respectively (ophthalmic solution 1 contained 0.5% CLZ, and ophthalmic solution 2 contained 0.01% CLZ).

In addition, to 100 mL of purified water were added 100 mg of cilostazol and 20 g of HP-β-CD, and the mixture was stirred until cilostazol was completely dissolved, to prepare 0.1% CLZ solution (20% HP-β-CD). The solution was frozen at −80° C., and then lyophilized. To 1.005 g of the lyophilizate was added 10 mL of physiological saline, and the solution was filtrated for sterilization to prepare 0.05% CLZ control ophthalmic solution. And the control solution was diluted with physiological saline so that the concentration of CLZ should be half, to prepare 0.025% CLZ control ophthalmic solution. (The above concentrations are shown as weight/volume %.)

(Comparative Experiment of Manufacturing Method)

To cilostazol suspension (0.5%, suspended in physiological saline) was added HP-β-CD powder so that the final concentration of the HP-β-CD should be 5-20%, and the mixture was completely dissolved (the procedure is termed as "dissolving method (1)"). On the contrary, to HP-β-CD solution (5-20%, dissolved in physiological saline) was added cilostazol powder (final concentration: 0.5%), and the mixture was completely dissolved (the procedure is termed as "dissolving method (2)"). Both the above solutions were stirred at 25° C. for 24 hours under the shade, then filtrated with membrane filter (pore size: 0.2 μm), and compared about the solubility of the solutions. Although both the solutions had the same composition, the solubility of cilostazol derived from dissolving method (1) tended to increase more (i.e., superior clathration) than that of dissolving method (2), as shown in FIG. 1. Actually, it needed 10 minutes' stirring for the solution derived from dissolving method (1) to reach the state of the dissolution curve shown in FIG. 1. However, the solution derived from dissolving method (2) which was stirred for 10 minutes exhibited a low solubility in only one fifth or less of the solubility shown in FIG. 1. (The above concentrations are shown as weight/volume %.)

(Dissolution Experiment of Cilostazol•Nano (Nano-CLZ))

CLZ and an excipient were mixed in a ratio of about 80%: 20% to give a nano-CLZ powder. To a nano-CLZ suspension (0.5% CLZ suspension: which was prepared by suspending 120 mg of the nano-CLZ powder in 20 mL of purified water), HP-β-CD powder was added and the mixture was dissolved so that the final concentration of HP-β-CD should be 5-20% (dissolving method (1)); while 120 mg of the nano-CLZ powder was added to a HP-β-CD solution (which was prepared by dissolving HP-β-CD in purified water so that the final concentration of HP-β-CD should be 5-20%), and the mixture was dissolved (the final concentration of CLZ is 0.5%) (dissolving method (2)). Both the above solutions were stirred at 25° C. for 24 hours under the shade, then filtrated with membrane filter (pore size: 0.2 μm), and compared about the solubility of the solutions.

Figure 2:
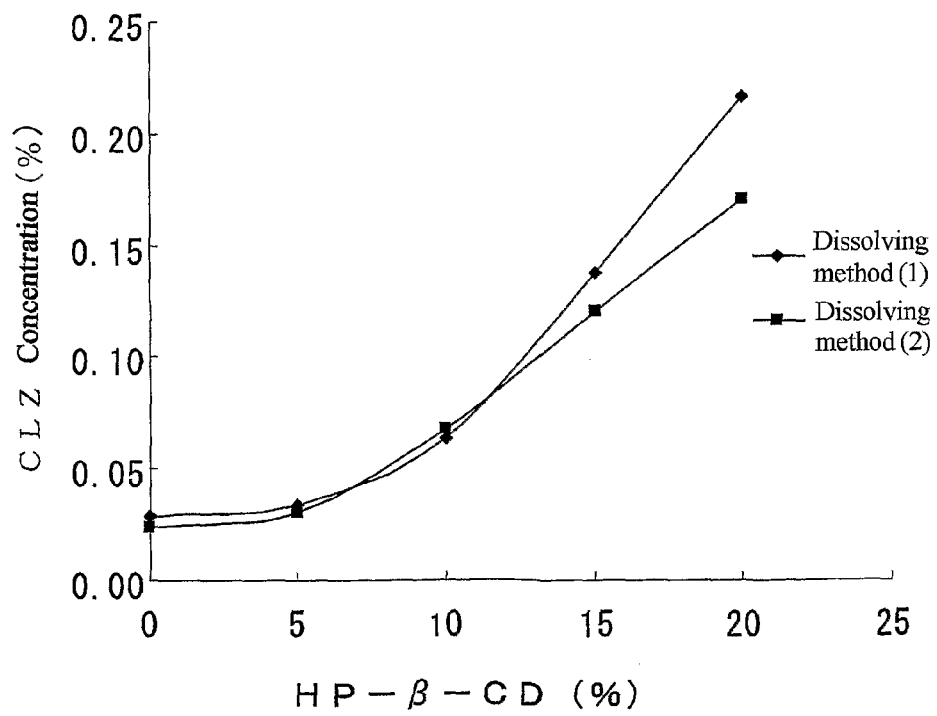
FIG. 2 shows the difference of cilostazol solubility depending on each dissolving method of the ophthalmic clathrate drug of cilostazol (nano-CLZ) in cyclodextrin.

Although both the solutions had the same composition, the solubility of cilostazol derived from dissolving method (1) tended to increase more (i.e., superior clathration) than that of dissolving method (2), as shown in FIG. 2. Actually, it needed 30 minutes' stirring for the solution derived from dissolving method (1) to reach the state of the dissolution curve shown in FIG. 2. However, the solution derived from dissolving method (2) which was stirred for 30 minutes exhibited a low solubility in only half or less of the solubility shown in FIG. 2. (The above concentrations are shown as weight/volume %.)

The particle size of nano-CLZ suspension prepared with purified water was measured with a particle size measuring device by dynamic laser light scattering: Sub-micron Particle Analyzer Model N4 SD (Coulter) and the results are shown as follows.

Nano-CLZ suspension: 251±20 nm

Filtrate (membrane filter, pore size: 0.2 μm): 181±47 nm (Pharmacological Experiment 1)

Figure 3:
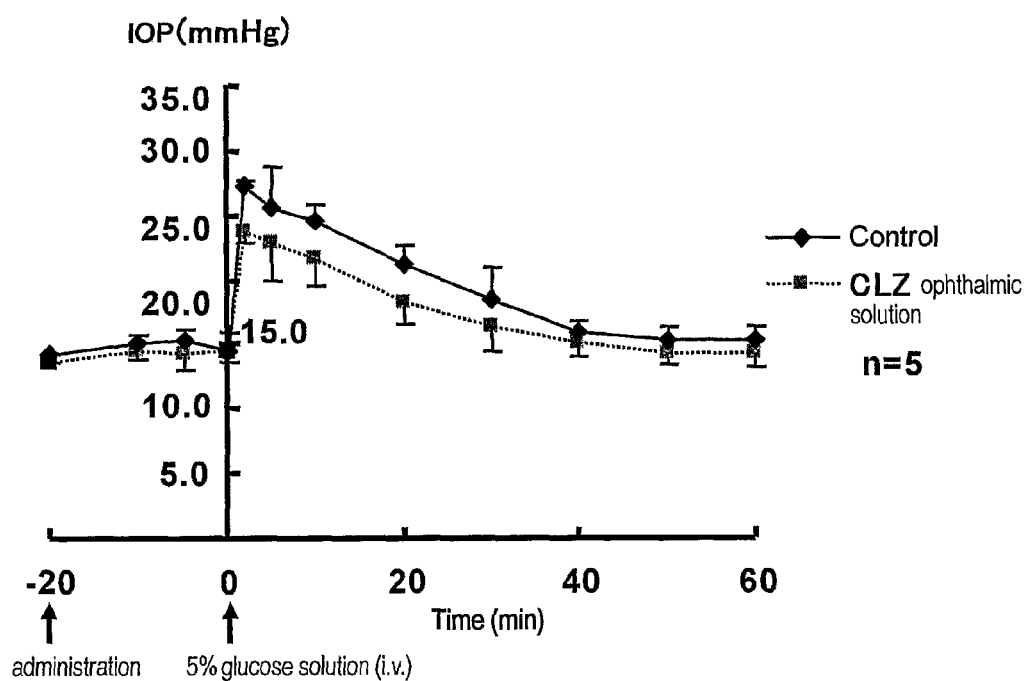
FIG. 3 shows the difference of intraocular pressure (IOP) of rabbits with/without the administration of the CLZ ophthalmic drug.
Figure 4:
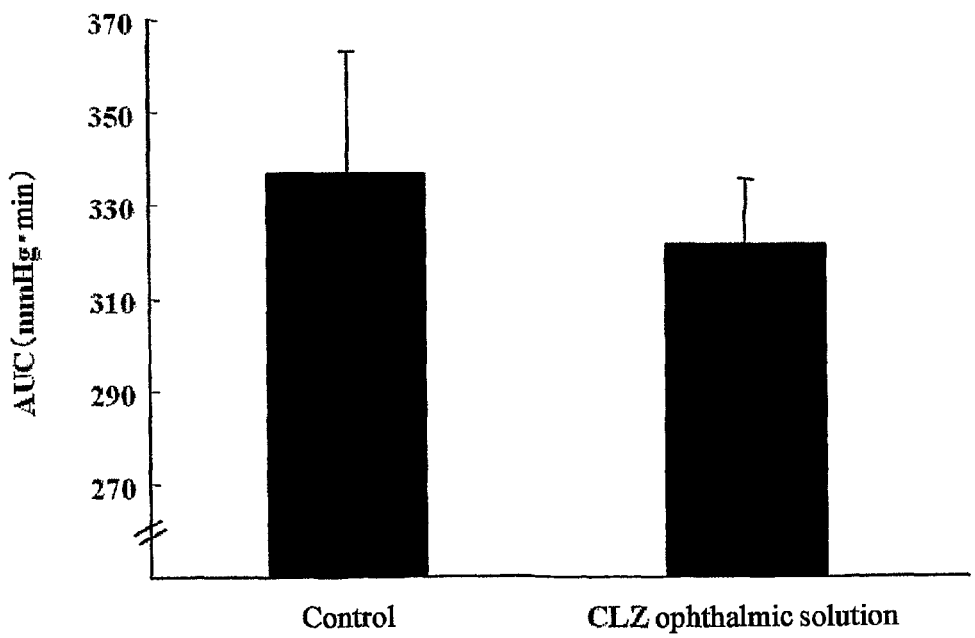
FIG. 4 shows the difference of intraocular pressure (IOP) of rabbits with/without the administration of the CLZ ophthalmic drug as AUC method.

A decreasing action of intraocular pressure was measured. Benoxil ophthalmic solution was dropped on both eyes of a male white rabbit for anesthesia. To one of the eyes was administrated 50 μL of the ophthalmic solution of clathrate compound of 0.05% cilostazol (CLZ) in the cyclodextrin. To the other eye was dropped 50 μL of 10% HP-β-CD solution as a control solution. After 20 minutes, 5% glucose solution was injected to auricular veins of the male white rabbit (15 mL/kg) within 30 seconds in order to transiently raise the intraocular pressure. 20 Minutes before the administration to 60 minutes after the administration, each intraocular pressure was measured at a regular interval. The results are shown in FIG. 3. It was shown that the intraocular pressure of the eye wherein the CLZ ophthalmic drug was administrated was totally lowered compared with the control one. FIG. 4 shows AUC about the intraocular pressure-time curve during the measurement period, which obviously indicates that the intraocular pressure of the eye wherein the CLZ ophthalmic drug was administrated was lowered compared with the control one. (The above concentrations are shown as weight/volume %.)

(Pharmacological Experiment 2)

Figure 5:
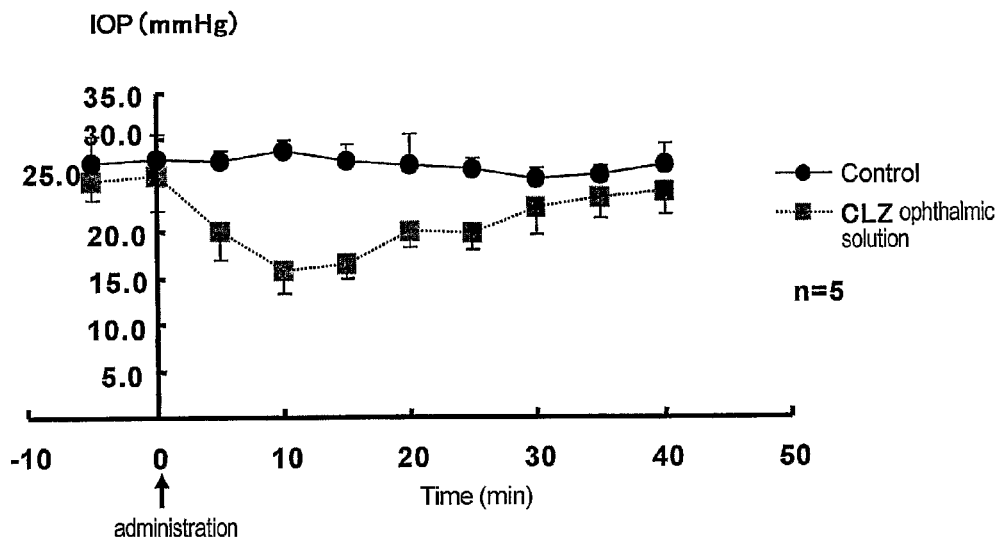
FIG. 5 shows the difference of intraocular pressure (IOP) between rabbits with the administration of the CLZ ophthalmic drug or the control under the shade.
Figure 6:
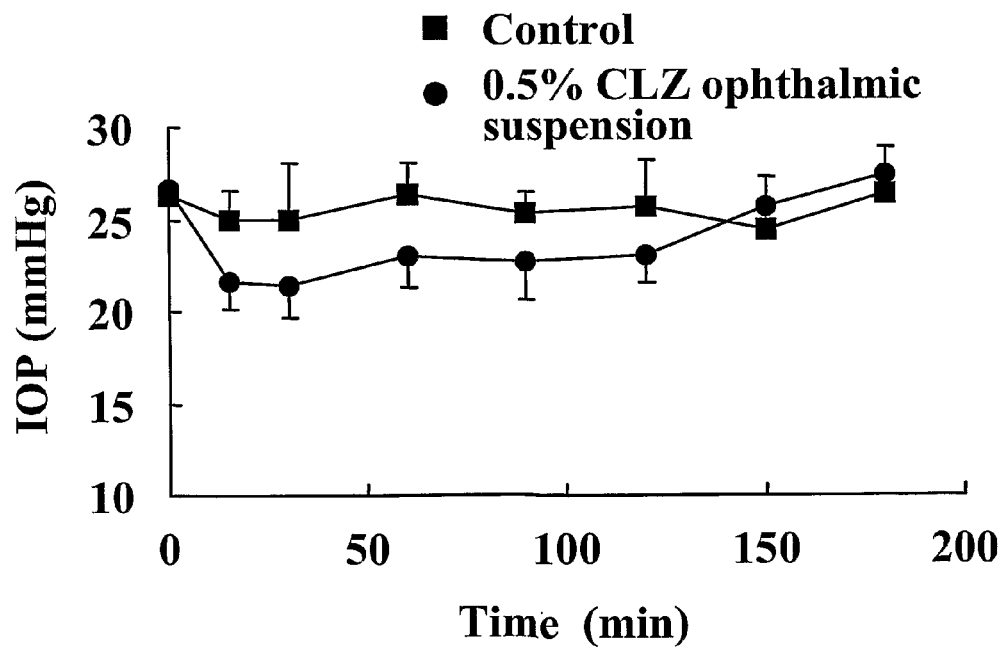
FIG. 6 shows the difference of intraocular pressure (IOP) between rabbits with the administration of the CLZ (nano-CLZ) ophthalmic drug or the control under the shade.

Under the shade, Benoxil ophthalmic solution was dropped on both eyes of a male white rabbit for anesthesia. To the right eye was administrated 50 μL of the ophthalmic solution of clathrate compound of 0.05% CLZ in cyclodextrin which was prepared in Example 1. To the left eye was dropped 50 μL of 10% HP-β-CD solution as a control solution. 5 Minutes before the administration to 30 minutes after the administration, each intraocular pressure was measured at a regular interval. The same experiment using the ophthalmic solution 1 contained 0.5% CLZ which were prepared in Example 2 (ophthalmic solution 1) was also carried out. In the both experiments, it was found that the intraocular pressure of the right eye wherein the CLZ ophthalmic drug was administrated was lowered compared with the left eye wherein only the cyclodextrin was administrated (See FIG. 5 for the ophthalmic solution of Example 1 and FIG. 6 for the ophthalmic solution of Example 2). (The above concentrations are shown as weight/volume %.)

In Vitro Experiment of Corneal Penetration Using Rabbits (1) Preparation of Buffer: HEPES (+Glc) Buffer Solution HEPES (final concentration: 10 mM), $NaCl_2$ (136.2 mM), KCl (5.3 mM), $K_2HPO_4$ (1.0 mM), $CaCl_2.H_2O$ (1.7 mM), and glucose (5.5 mM) were added in turn into a vessel and dissolved, and then pH of the solution was adjusted to 7.4 with 1N NaOH, and the solution was filtrated over a membrane filter Minisart CE (SARTORIUS, 0.2 μm).

(2) Experiment of Corneal Penetration

After male Datch rabbits were euthanized by injecting a lethal dose of pentobarbital and air to auricular veins thereof, the eyeballs thereof were carefully extirpated and the cornea part thereof leaving about 1-2 mm of the sclera was cut down taking care to not to be hurt. The cornea was attached on a corneal penetration cell made of acrylic resin. To the reservoir side (aqueous humor) was added 3.0 mL of the above isotonic HEPES buffer solution (pH 7.4), and to the donor side (aqueous tear) was added 3.0 mL of each CLZ ophthalmic solution prepared above, which were heated at 35° C. The corneal penetration cell was kept at 35° C. in a thermostat bath. 15 Minutes to 6 hours after the test started, the sampling was carried out from the reservoir side in an amount of every 10 μL at a time at a regular interval. The sample was measured by a HPLC method using methylphenyloin as an internal standard to analyze the amount of CLZ which got through the cornea.

Figure 7:
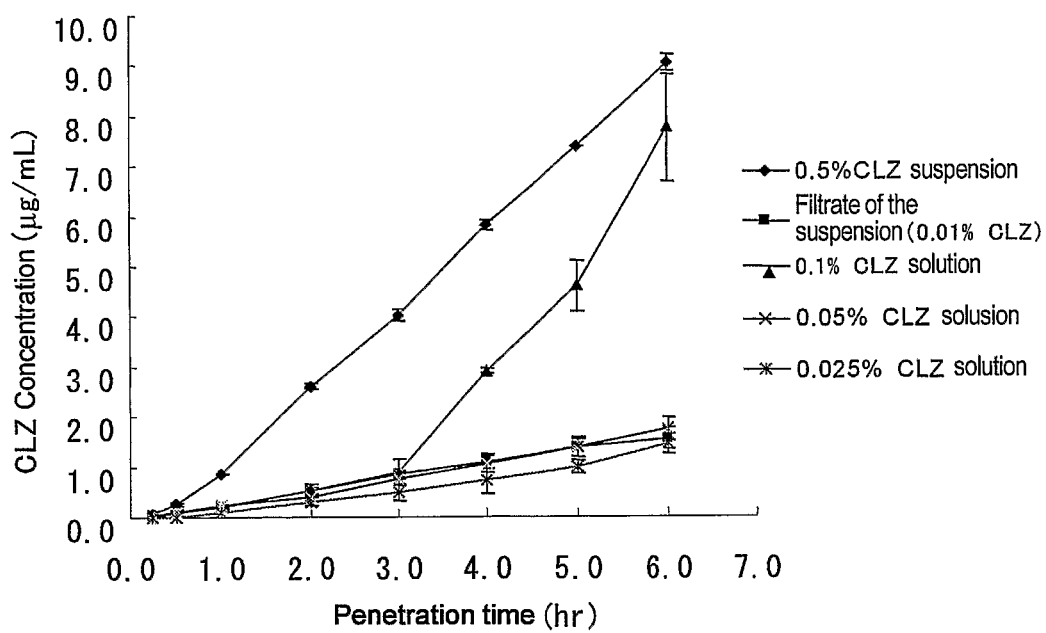
FIG. 7 shows the amount of corneal penetration of rabbits depending on the concentration of CLZ together with the time course.

The results are shown in FIG. 7. It was found that the corneal penetration was enhanced depending on the concentration of CLZ, i.e., in the order of ophthalmic solution 1 (0.5% CLZ suspension), 0.1% CLZ solution, 0.05% CLZ solution, ophthalmic solution 2 (filtrate of the suspension: 0.01% CLZ), and 0.025% CLZ solution.

The invention claimed is:

1. A method for treating glaucoma which comprises administering an ophthalmic composition comprising 0.005 to 1% (w/v) of a carbostyril derivative or a salt thereof of the general formula:

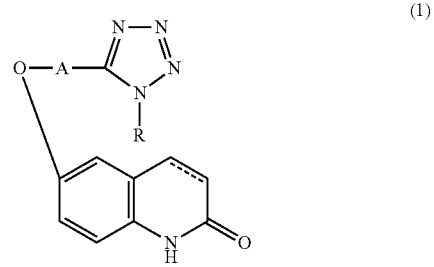

(1)

wherein A is a $C_1$-$C_6$ alkylene group, R is a $C_3$-$C_8$ cycloalkyl group, and the bonding between 3- and 4-positions of the carbostyril skeleton is a single bond or a double bond, and a cyclodextrin to a patient in need of such treatment, wherein the ophthalmic composition is administered as an eye drop or ointment.

2. The method of claim 1, wherein the carbostyril derivative is 6-[4-(1-cyclohexyl-1H-tetrazol-5-yl)butoxy]-3,4-dihydrocarbostyril or a salt thereof.

3. The method of claim 1 or 2, wherein the cyclodextrin is 2-hydroxypropyl-β-cyclodextrin.

\* \* \* \* \*

UNITED STATES PATENT AND TRADEMARK OFFICE
CERTIFICATE OF CORRECTION

PATENT NO. : 8,686,001 B2
APPLICATION NO. : 12/671545
DATED : April 1, 2014
INVENTOR(S) : Okamoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1095 days.

Signed and Sealed this
Thirtieth Day of May, 2017

Michelle K. Lee
*Director of the United States Patent and Trademark Office*